Figure 1:
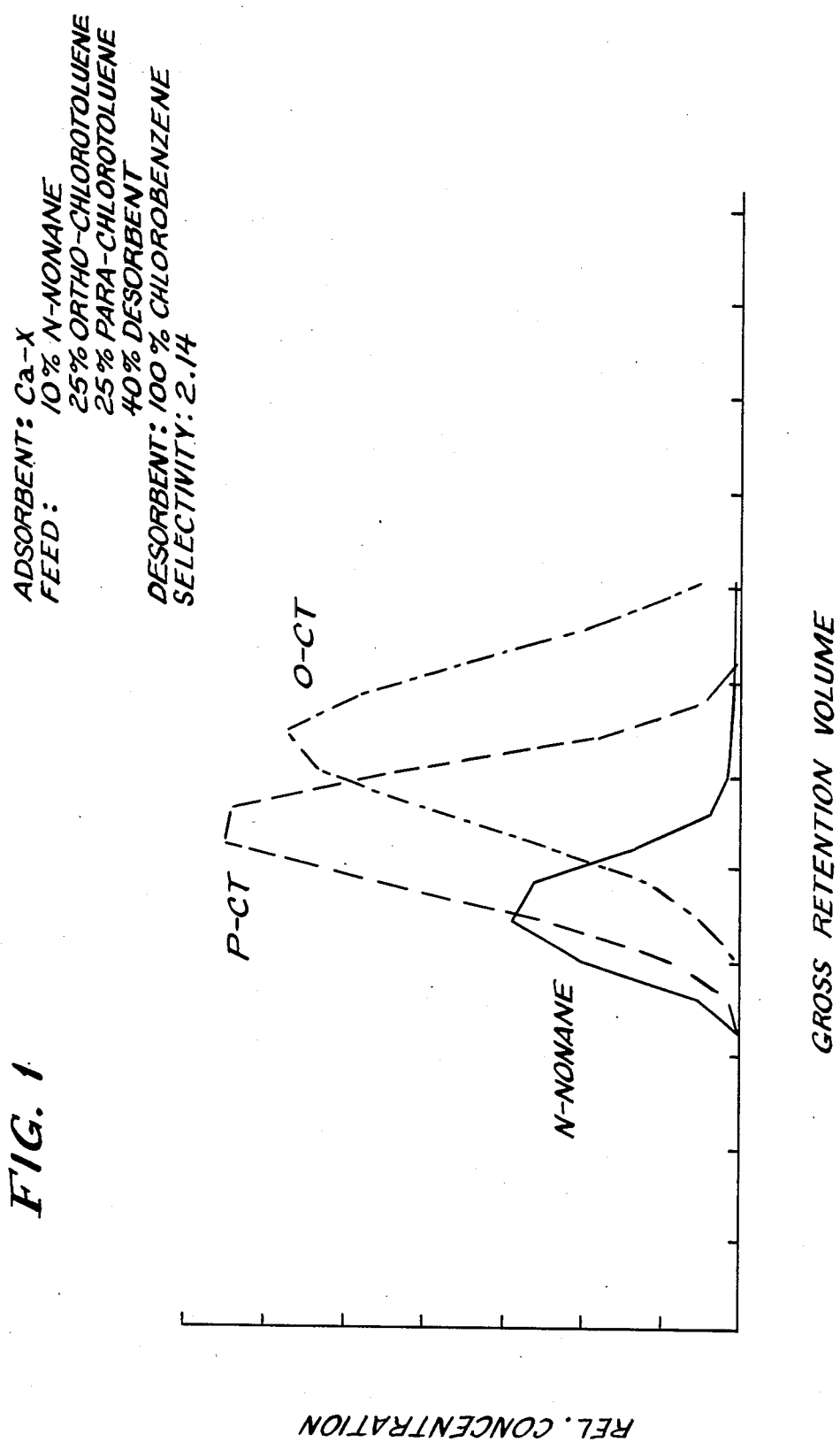

United States Patent [19]

Zinnen et al.

[11] Patent Number: 4,794,202
[45] Date of Patent: Dec. 27, 1988

[54] PROCESS FOR SEPARATING HALOGEN SUBSTITUTED TOLUENE ISOMERS

[75] Inventors: Hermann A. Zinnen, Evanston; Thad S. Franczyk, Skokie, both of Ill.

[73] Assignee: UOP Inc., Des Plaines, Ill.

[21] Appl. No.: 723,582

[22] Filed: Apr. 15, 1985

[51] Int. Cl.$^4$ .......................................... C07C 17/38
[52] U.S. Cl. ................................................ 570/211
[58] Field of Search ........................................ 570/211

[56] References Cited

U.S. PATENT DOCUMENTS

| 2,958,708 | 11/1960 | Fleck et al. | 260/650 |
| 2,985,589 | 5/1961 | Broughton et al. | 210/34 |
| 3,201,491 | 8/1965 | Stine et al. | 260/676 |
| 3,265,750 | 8/1966 | Peck et al. | 260/666 |
| 3,510,423 | 5/1970 | Neuzil et al. | 208/310 |
| 3,626,020 | 3/1969 | Neuzil | 260/674 SA |
| 3,663,638 | 5/1972 | Neuzil | 260/674 SA |
| 3,665,046 | 5/1972 | DeRosset | 260/674 SA |
| 3,668,266 | 6/1972 | Chen et al. | 260/674 |
| 3,686,343 | 8/1972 | Bearden, Jr. et al. | 260/674 SA |
| 3,700,744 | 10/1972 | Berger et al. | 260/668 A |
| 3,734,974 | 5/1973 | Neuzil | 260/674 SA |
| 3,997,620 | 12/1976 | Neuzil | 260/674 SA |
| 4,254,062 | 3/1981 | Wambach et al. | 570/211 |

FOREIGN PATENT DOCUMENTS

| EP99161 | 1/1984 | European Pat. Off. | 570/211 |
| 3327146 | 7/1983 | Fed. Rep. of Germany . | |
| 1188482 | 1/1982 | Japan . | |
| 31627 | 2/1982 | Japan | 570/211 |
| 5044083 | 3/1983 | Japan . | |

Primary Examiner—Werren B. Lone
Attorney, Agent, or Firm—Thomas K. McBride; John F. Spears, Jr.; Jack H. Hall

[57] ABSTRACT

A process for separating the para and ortho isomers of a halogen substituted toluene from a feed mixture of the same. Separation of the isomers is effected by selective adsorption and desorption and is susceptible to various flow schemes for performing continuous adsorptive separations. The process uses an X type zeolite adsorbent having calcium, barium, potassium, or combinations thereof as cations and a mixed desorbent containing chlorobenzene and/or bromobenzene and alicyclic hydrocarbons.

11 Claims, 10 Drawing Sheets

PROCESS FOR SEPARATING HALOGEN SUBSTITUTED TOLUENE ISOMERS

BACKGROUND OF THE INVENTION

1. Field of the Invention

The field of art to which this invention pertains is the solid bed adsorptive separation of halogen substituted aromatic hydrocarbons. More specifically, the invention relates to a process for separating para and ortho isomers of halotoluenes employing as the adsorbent X or Y zeolites containing alkali or alkaline earth metal cations.

2. Background Information

A wide variety of halogenating agents, catalysts and reaction conditions are used in processes for halogenating toluene. Thus far the isomers of chlorotoluene have been of the most interest, accordingly, most information related to the halogenated toluenes are in the context of the chlorotoluene isomers. Therefore in looking at the preparation and specific properties of halotoluene isomers, specific reference will be made to chlorotoluene. However, the procedures and information related to the other halogen substituents is similar in most respects. In regard to chlorotoluene isomers, most recent work has attempted to develop means for increasing the yield of the para isomer which has greater commercial significance. Mixtures of monochlorotoluenes are obtained by chlorination with certain Lewis catalysts including the chlorides of aluminum, tin, titanium and zirconium. Through these procedures the mixture of monochlorotoluenes will contain more than 70% of the ortho isomer. A para isomer content in the range of 45–55% is obtainable through the use of metal sulfide cocatalyst systems containing metal salts and sulfur, inorganic sulfides or divalent organic sulfur compounds. Other methods of obtaining monochlorotoluene isomers include the noncatalytic nuclear chlorination of toluene in various solvents, the reaction of toluene with chlorinating agent comprising certain Lewis acid halides and the use of hydrogen chloride as a chlorinating agent in both liquid and vapor phase systems. When preparing monochlorotoluene isomers by direct chlorination it has been found that less than 1% of the isomers produced will comprise the meta isomer. Consequently feedstocks for this invention will often contain a small proportion of the meta isomer which is not removed prior to the separation of the para and ortho isomers.

Separation of ortho and parahalotoluenes is difficult due to the close boiling point range of these isomers. In order to accomplish a separation of these isomers by fractionation it is necessary to use a high efficiency isomer separation column. This invention simplifies the separation procedure by providing a more effective adsorptive separation method.

Crystalline alumina silicates are commonly used in the separation art to perform adsorptive separations. Example of such separations in the field of hydrocarbons are disclosed in U.S. Pat. Nos. 2,985,589 and 3,201,491. In these patents normal paraffins are separated from branched chain paraffins using a type A zeolite. U.S. Pat. Nos. 3,265,750 and 3,510,423 are more specifically directed to the use of faujasites to separate olefinic hydrocarbons from paraffinic hydrocarbons. Adsorbents such as these rely on physical size differences in the molecules to perform the separation wherein the smaller or normal hydrocarbons are allowed to pass into cavities within the zeolite adsorbent which the larger or branched chain molecules cannot enter. The use of X or Y zeolites to separate individual hydrocarbon isomers is also well known. For example, U.S. Pat. Nos. 3,626,020, 3,663,638, 3,665,046, 3,668,266, 3,686,343, 3,700,744, 3,734,974, and 3,997,620 demonstrate the use of zeolitic adsorbents in the separation of the para isomer of alkyl substituted monocyclic aromatics from other isomers particularly paraxylene from other xylene isomers.

Turning now specifically to the separation of substituted aromatic isomers there are several relevant patent publications. The separation of substituted benzene isomers using a faujasite containing silver or copper cations is taught in German Patent DE No. 3327146. More specifically related to the present invention are the public disclosures related to Japanese Patent Application Nos. 11,884/82 and 50,440/83. Both of these patent applications deal with the separation of metachlorotoluene from a mixture of chlorotoluene isomers. In the first application metachlorotoluene is adsorbed on a Y zeolite containing silver and potassium cations. The second application teaches the adsorption of metachlorotoluene on a Y zeolite adsorbent containing sodium and copper cations as essential components.

With suitably active catalysts it is possible to obtain halogenated toluene isomers with only trace amounts of side chain halogenated products. Nevertheless there would usually be a small percentage of reactive halides which are left over from the preparation of the isomers. Traces of halides, in particular chloride in the product, can be highly reactive with any transition metal ions that are exchanged into the zeolite adsorbent. Therefore in light of this likely contamination it is highly desirable to avoid the use of ions such as copper or silver which will readily react with the traces of chloride or other halides that may be present in the feedstock.

The separation of halogenated aromatic isomers using zeolites containing alkali or alkaline earth metal cations is disclose in U.S. Pat. No. 2,958,708. This reference includes examples demonstrating the relatively low selectivity of a calcium exchanged zeolite for orthochlorotoluene over parachlorotoluene using a chlorobenzene displacement fluid.

In contradistinction to the prior art, the present invention resides in a particular combination of adsorbents and desorbents which substantially increases the selectivity of the adsorbent for one halogenated toluene isomer over another.

SUMMARY OF THE INVENTION

In brief summary the invention is a process for separating the para and ortho isomers of a halotoluene in which the halogen is chlorine or bromine from a feed mixture comprising a mixture of the isomers. The process comprises contacting the para and ortho isomers at adsorption conditions with an adsorbent comprising an X zeolite containing barium, calcium, or potassium cations or combinations thereof at cation exchange sites. After contact with the adsorbent the unadsorbed portion of the feed is removed and the adsorbed component is recovered using a mixture comprising chlorobenzene and/or bromobenzene and an alkane as a desorbent. In a more specific embodiment, the desorbent comprises chlorobenzene in admixture with isooctane or normal hexane.

Other embodiments of the present invention encompass specific feed mixtures, desorbent compositions, flow schemes and operating conditions, all of which are hereinafter disclosed in the following discussion of the present invention.

Preferred feed mixtures for this process contain substantial quantities of the para and ortho isomers of monohalotoluenes. The primary use of halotoluenes is as chemical intermediates. In particular mono- and dichlorotoluenes are used in the manufacture of pesticides, dye stuffs, pharmaceuticals and peroxides. Halogen substituted toluenes are also employed as solvents.

To separate the ortho or para isomer from a mixture of monochlorotoluenes or monobromotoluenes in accordance with the present invention, the mixture is contacted with the previously mentioned class of adsorbents and the ortho or para isomer is selectively adsorbed and retained by the adsorbent while the other relatively unadsorbed isomer is removed from the interstitial void spaces between the particles of adsorbent in the surface of adsorbent. The adsorbent containing the more selectively adsorbed isomer is referred to as a "rich" adsorbent. The more selectively adsorbed isomer is then recovered from the rich adsorbent by contacting the rich adsorbent with a desorbent material.

In the process of this invention, it has been found that particular desorbent materials comprising mixtures of chlorobenzene and/or bromobenzene and alkanes will increase overall selectivity in the adsorptive separation of bromo or chlorotoluene isomers with the adsorbents herein described. Of the possible alkanes which may be used in the desorbents, those having less than 9 carbon atoms are most useful due to their lower boiling point properties. Of these hydrocarbons $C_8$–$C_4$ alkanes are preferred. Particularly preferred hydrocarbons include normal hexane and isooctane. As an additional advantage the lower boiling point properties of branched chain hydrocarbons with respect to their paraffinic counterparts makes the former components easier to separate from products. Moreover, suitable desorbents will contain no less than ten volume percent of the halogenated benzene and hydrocarbon components with a higher volume percent of the hydrocarbon component being preferred. A particularly preferred range of hydrocarbon constituents is from 60 to 90 volume percent.

DESCRIPTION OF THE INVENTION

The adsorbent materials of this invention comprise type X crystalline aluminosilicates having barium, calcium, potassium or combinations thereof as cations at cation exchange sites. The type X crystalline aluminosilicates or zeolites can be further classified as faujasites. As in the general case of all zeolites, these crystalline compounds are described as a three-dimensional network of fundamental structural units consisting of silicon-centered $SiO_4$ and aluminum-centered $AlO_4$ tetrahedra interconnected by a mutual sharing of apical oxygen atoms. The space between the tetrahedra is occupied by water molecules and subsequent dehydration or partial dehydration results in a crystal structure interlaced with channels of molecular dimension.

Thus, the crystalline aluminosilicates are often referred to as molecular sieves and separations performed with molecular sieves are generally thought to take place by a physical "sieving" of smaller from larger molecules appearing in the feed mixture. In the separation of aromatic hydrocarbon isomers, however, the separation of the isomers apparently occurs because of differences in electrochemical attraction of the different isomers and the adsorbent rather than on pure physical size differences in the isomer molecules.

The prior art has generally recognized that adsorbents comprising X and Y zeolites can be used in certain adsorptive separation processes. These zeolites are described and defined in U.S. Pat. Nos. 2,883,244 and 3,120,007 respectively, incorporated herein by reference thereto. The X zeolite in the hydrated or partially hydrated form can be represented in terms of mole oxides as shown in the formula below:

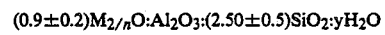

$$(0.9\pm0.2)M_{2/n}O:Al_2O_3:(2.50\pm0.5)SiO_2:yH_2O$$

where "M" represents at least one cation having a valence of not more than 3, "n" represents the valence of "M", and "y" is a value up to about 9 depending upon the identify of "M" and the degree of hydration of the crystal. As noted from the formula the $SiO_2/Al_2O_3$ mole ratio of X zeolite is 2.5±0.5. The cation "M" may be one or more of a number of cations such as a hydrogen cation, an alkali metal cation, or an alkaline earth cation, or other selected cations, and is generally referred to as an exchangeable cationic site. As the X zeolite is initially prepared, the cation "M" is usually predominantly sodium, that is, the major cation at the exchangeable cationic sites is sodium and the zeolite is therefore referred to as a sodium-X zeolite. Depending upon the purity of the reactants used to make the zeolite, other cations mentioned above may be present, however, as impurities.

Cations occupying exchangeable cationic sites in the zeolite may be replaced with other cations by ion exchange methods well known to those having ordinary skill in the field of crystalline aluminosilicates. By such methods, the sodium cations and any nonsodium cations which might be occupying exchangeable sites as impurities in a sodium-X zeolite can be partially or essentially completely replaced with other cations. Although there are many possible cations which can be exchanged into the zeolite material, it is important to choose the cation that will retain the balancing function within the zeolite structure. Hence many transition metal cations such as copper and silver are poor exchange cation since they tend to revert to their elemental state. It is essential that the zeolite used in the process of our invention contain barium, calcium, potassium or combinations thereof as cations at exchangeable cationic sites.

Typically, adsorbents used in separation processes contain zeolite crystals and amorphous material. The zeolite will typically be present in the adsorbent in amounts ranging from about 75 wt. % to about 98 wt. % based on volatile free composition. Volatile free compositions are generally determined after the adsorbent has been calcined at 900° C. in order to drive off all volatile matter. The remainder of the adsorbent will generally be amorphous material such as silica, or silica-alumina mixtures or compounds, such as clays, which material is present in intimate mixture with the small particles of the zeolite material. This amorphous material may be an adjunct oof the manufacturing process for zeolite (for example, intentionally incomplete purification of either zeolite during its manufacture), or it may be added to relatively pure zeolite, but in either case its usual purpose is as a binder to aid in forming or agglomerating the hard crystalline particles of the zeolite. Normally, the adsorbent will be in the form of particles such as extrudates, aggregates, tablets, macrospheres or granules having a desired particle size range.

The adsorbent used in our process will preferably have a particle size range of about 16-40 mesh (Standard U.S. Mesh). It has been found that X zeolites with calcium, barium or potassium cations possess the selectivity requirements and other necessary requirements previously discussed and are therefore suitable for use in this process.

The terminology for adsorptive separation processes includes the terms "extract component" which is a type of compound or a compound that is more selectively adsorbed by the adsorbent and "raffinate component" which is a compound or type of compound that is less selectively adsorbed. In this process, either the ortho or para isomer is the extract component and the other nonextract isomer is a raffinate component. The term "raffinate stream" or "raffinate output stream" means a stream through which a raffinate component is removed from an adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product or a raffinate product at high recoveries, it will be appreciated that an extract component is never completely adsorbed by the adsorbent, nor is a raffinate component completely nonadsorbed by the adsorbent. Therefore, small amounts of a raffinate component can appear in the extract stream and likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of a more selectively adsorbed parahalotoluene to the concentration of a less selectively adsorbed orthohalotoluene will be highest in the extract stream, next highest in the feed mixture, and lowest in the raffinate stream. Likewise, the ratio of a less selectively adsorbed orthohalotoluene to a more selectively adsorbed parahalotoluene will be highest in the raffinate stream, next highest in the feed mixture, and the lowest in the extract stream.

The adsorption-desorption operations may be carried out in a dense fixed bed which is alternatively contacted with a feed mixture and a desorbent material in which case the process will be only semicontinuous. In another embodiment, generally referred to as a swing bed system, a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Moving bed or simulated moving bed flow systems, however, have a much greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. In such a system, it is the progressive movement of multiple liquid access points down a molecular sieve chamber that simulates the upward movement of molecular sieve contained in the chamber. Reference can also be made to D. B. Broughton's U.S. Pat. No. 2,985,589, in which the operating principles and sequence of such a flow system are described, and to a paper entitled, "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the cocurrent high efficiency simulated moving bed process disclosed in U.S. Pat. No. 4,402,832 to Gerhold, incorporated by reference herein in its entirety.

A desorbent material is any fluid substance capable of removing a selectively adsorbed feed component from the adsorbent. Generally, in a swing-bed system in which the selectively adsorbed feed component is removed from the adsorbent by a purge stream, desorbent material selection is not too critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to ensure liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract component from displacing the desorbent material in a following adsorption cycle. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for the extract components with respect to the raffinate component. Desorbent materials to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high. It is therefore in the continuous separation processes where the previously described class of preferred desorbents will offer the greatest advantages.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically the concentration of desorbent material in the extract product and the raffinate product will be less than about 5 volume percent and more preferably less than about 1 volume percent. The separation means will typically be a fractionation column, the design and operation of which is well known to the separation art.

Although both liquid and vapor phase operations can be used in many adsorptive separation processes, liquid-phase operation is preferred for this process because of the lower temperature and energy requirements and because of the higher yields of an extract product that can be obtained with liquid-phase operation over those obtained with vapor-phase operation. Adsorption conditions will include a temperature range of from about 20° C. to about 250° C., with about 50° C. to about 200° C. being more preferred, and a pressure sufficient to maintain liquid phase. Desorption conditions will include the same range of temperatures and pressure as used for adsorption conditions.

The size of the units which can utilize the process of this invention can vary anywhere from those of pilot-plant scale (see for example U.S. Pat. No. 3,706,812) to those of commercial scale and can range in flow rates from as little as a few cc an hour up to many thousands of gallons per hour.

Certain characteristics of adsorbents are recognized in the prior art as highly desirable, if not absolutely necessary, to the successful operation of a selective adsorption process. Among such characteristics are: adsorptive capacity for some volume of an extract component per volume of adsorbent; the selective adsorption of an extract component with respect to a raffinate component and the desorbent material; and, sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B) for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases respeciively. The equilibrium conditions are determined when the feed passing over a bed of adsorbent does not change composition after contacting the bed of adsorbent. In other words, there is no net transfer of material occurring between the unadsorbed and adsorbed phases.

Where selectivity of two components approaches 1.0 there is no preferential adsorption of one component by the adsorbent with respect to the other; they are both adsorbed (or nonadsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material, or in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate, a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a nonadsorbed paraffinic tracer (n-nonane for instance) and the particular halogen substituted toluene isomers all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternately, effluent samples can be collected periodically and later analyzed separately by gas chromatography.

From information derived from the chromatographic traces, adsorbent performance can be rated in terms of capacity index for an extract component, selectivity for one hydrocarbon with respect to another, and the rate of desorption of an extract component by the desorbent. The capacity index may be characterized by the distance between the center of the peak envelope of the selectively adsorbed component and the peak envelope of the tracer component of some other known reference point. It is expressed in terms of the volume in cubic centimeters of desorbent pumped during this time interval. Selectivity, (B), for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

The following examples are presented for illustration purposes and more specifically are presented to illustrate the selectivity relationships that make the process of the invention possible. Reference to specific desorbent materials, feed mixtures and operating conditions is not intended to unduly restrict or limit the claims of this invention. The testing apparatus for each experiment was the above described pulse test device with gas chromatograph attached to the column effluent stream in order to determine the composition of the effluent material at given time intervals.

EXAMPLE I

In this experiment, two pulse tests were performed to evaluate the advantage of the present invention in separating orthochlorotoluene from parachlorotoluene.

Figure 2:
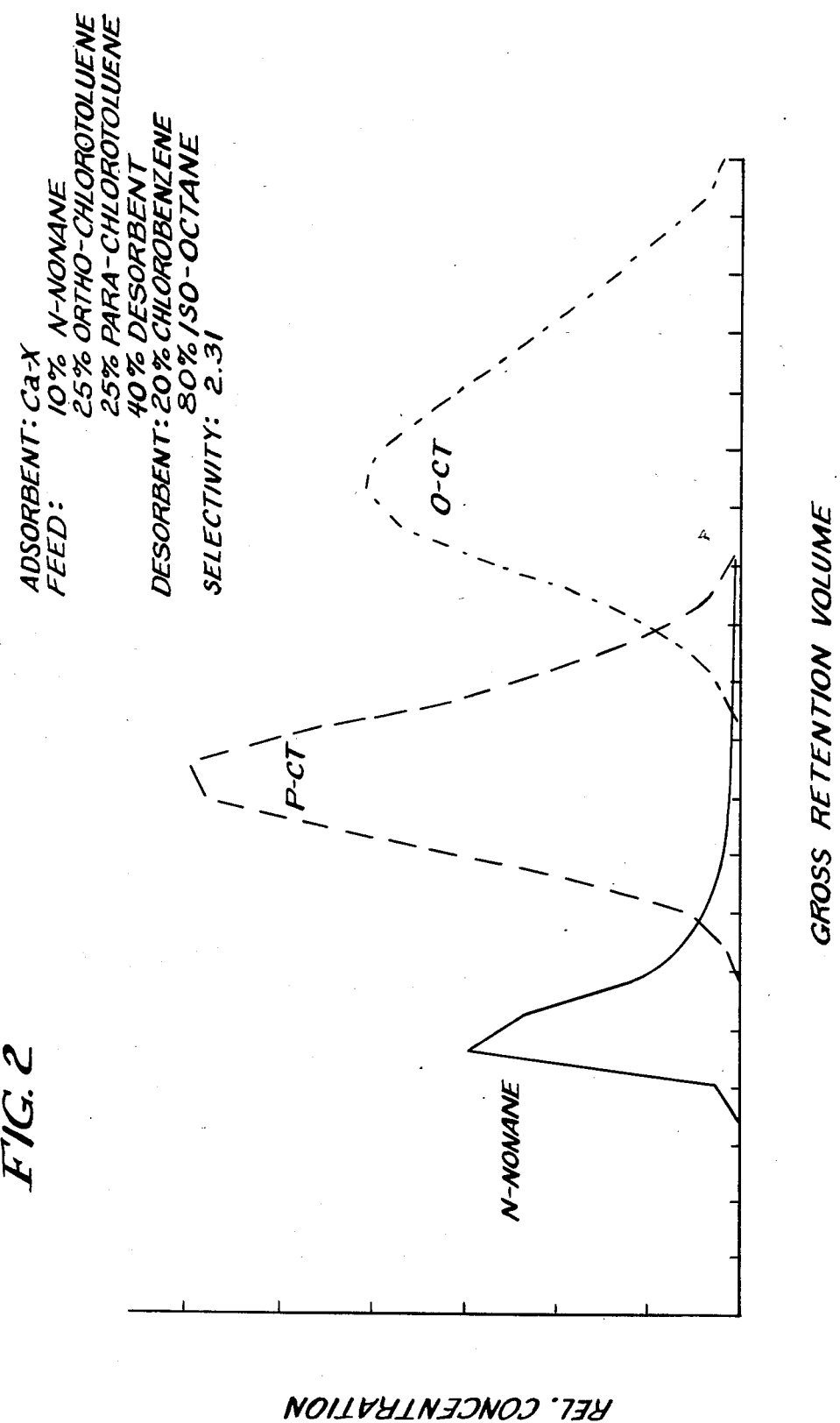

In the first pulse test, the column was filled with 70 cc of a type X zeolite having calcium cations at cation exchange sites and maintained at a temperature of 150° C. and a pressure sufficient to provide liquid-phase operations. The feed mixture employed or this test contained 25 vol. % orthochlorotoluene, 25 vol. % parachlorotoluene, 10 vol. % normal nonane and 40 vol. % desorbent material. The desorbent material was 100% chlorobenzene. The apparatus conditions and feedstock were the same for the second test with the only difference being in the case of a desorbent material made up of a mixture of 20 vol. % chlorobenzene and 80 vol. % isooctane. The operations taking place for each test were as follows. The desorbent material was run continuously at a nominal liquid hourly space velocity (LHSV) of 1 which amounted to about 1.2 cc per minute flow rate of desorbent. At some convenient time interval the desorbent was stopped and the feed mixture was run for a 1.66 minute interval at a rate of 1.2 cc per minute. The desorbent stream was then resumed at 1 LHSV and continued to pass into the adsorbent column until all of the feed components had been eluted from the column as determined by observing the chromatograph generated by the effluent material leaving the adsorption column. The sequence of operations usually takes about an hour. The 1.66 minute pulse of feed and subsequent desorption may be repeated in sequence as often as is desired. The chromatograph tracings obtained are shown in the attached FIGS. 1 and 2. Although the tracings of FIG. 1 representing Test 1 do show the occurrence of a separation wherein orthochlorotoluene is the selectively adsorbed component, a comparison of FIG. 2 shows a markedly improved separation with the use of the mixed desorbent of this invention. The improvement in performance obtained can also be expressed in terms of selectivity where the mixed desorbent increased the selectivity to a value of 2.31 from a value of 2.14 for the chlorobenzene desorbent alone.

EXAMPLE II

Figure 3:
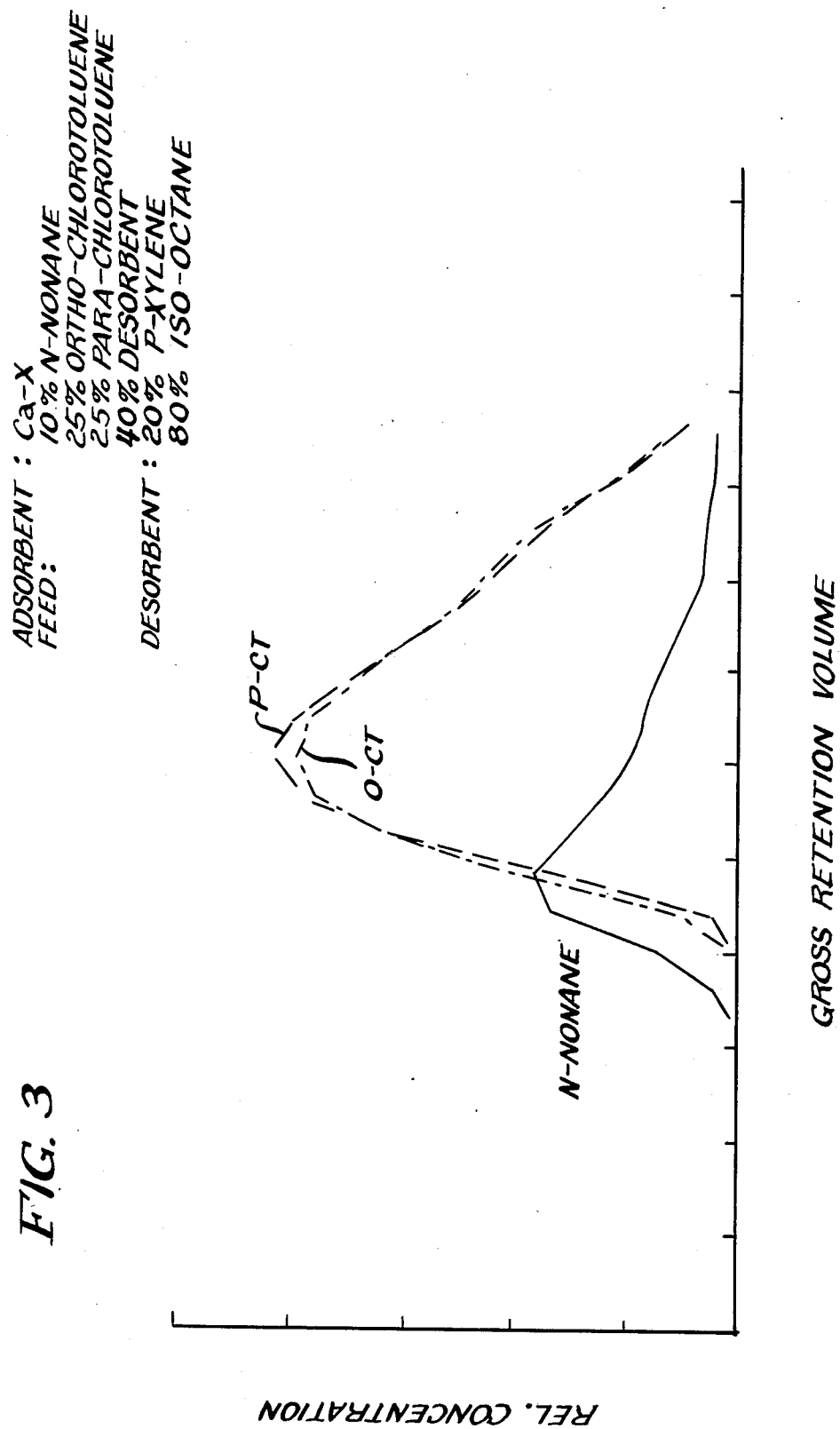

As additional evidence of the importance of proper desorbent selection in an adsorptive separation process an additional pulse test was performed with the same feed and under the same conditions of Example I. However, in this example, the desorbent material consisted of a mixture of 20 vol. % paraxylene and 80 vol. % isooctane. The results of this pulse test are presented graphically in FIG. 3. As illustrated by the Figure, no separation of the chlorotoluenes was achieved.

EXAMPLE III

In order to demonstrate the selective adsorption of the para isomer and the use of other adsorbents, additional pulse tests were performed with a feed mixture containing parachlorotoluene and orthochlorotoluene using a type X zeolite having barium and potassium cations at cation exchange sites.

For these pulse tests, the column was filled with 70 cc of the desired adsorbent and maintained at a temperature of 150° C. and a pressure sufficient to maintain liquid-phase operations. The feed mixture employed for each test contained about 5 vol. % of normal nonane, 25 vol. % orthochlorotoluene, 25 vol. % parachlorotoluene, and 45 vol. % desorbent material. The desorbent material for Test 4 was 20 vol. % chlorobenzene and 80 vol. % isooctane and the desorbent for Test 5 was 100 vol. % chlorobenzene. The operations taking place for these tests were as follows. The desorbent material was run continuously at a nominal liquid hourly space velocity (LHSV) of 1 which amounted to about 1.2 cc per minute flow rate of desorbent. At some convenient time interval the desorbent was stopped and the feed mixture was run for a 1.66 minute interval at a rate of 1.2 cc per minute. The desorbent stream was then resumed at 1 LHSV and continued to pass into the adsorbent column until all of the feed components had been eluted from the column as determined by observing the chromatograph generated by the effluent material leaving the adsorption column. The tracings obtained are shown in the attached FIGS. 4 and 5.

Figure 4:
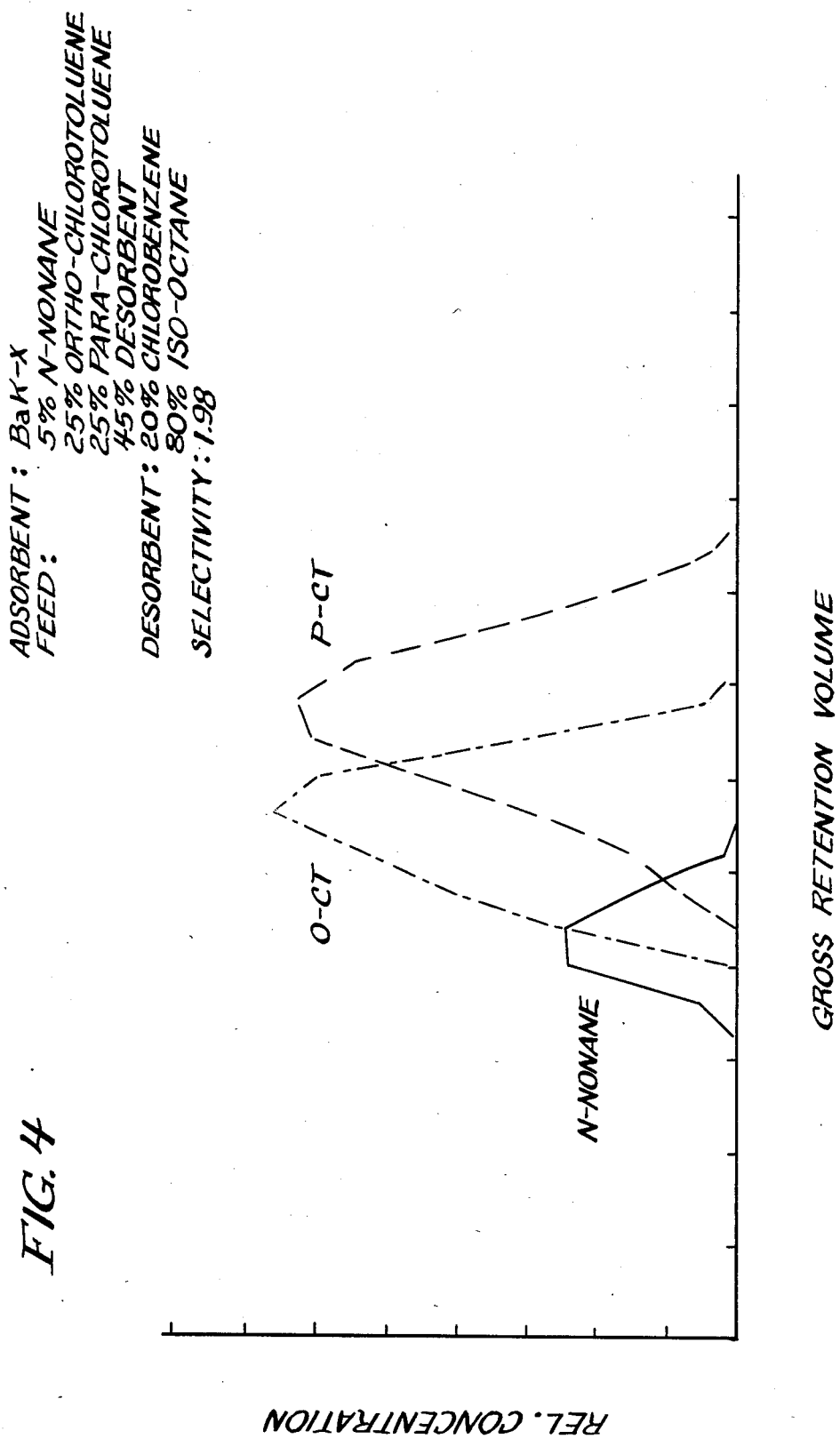
Figure 5:
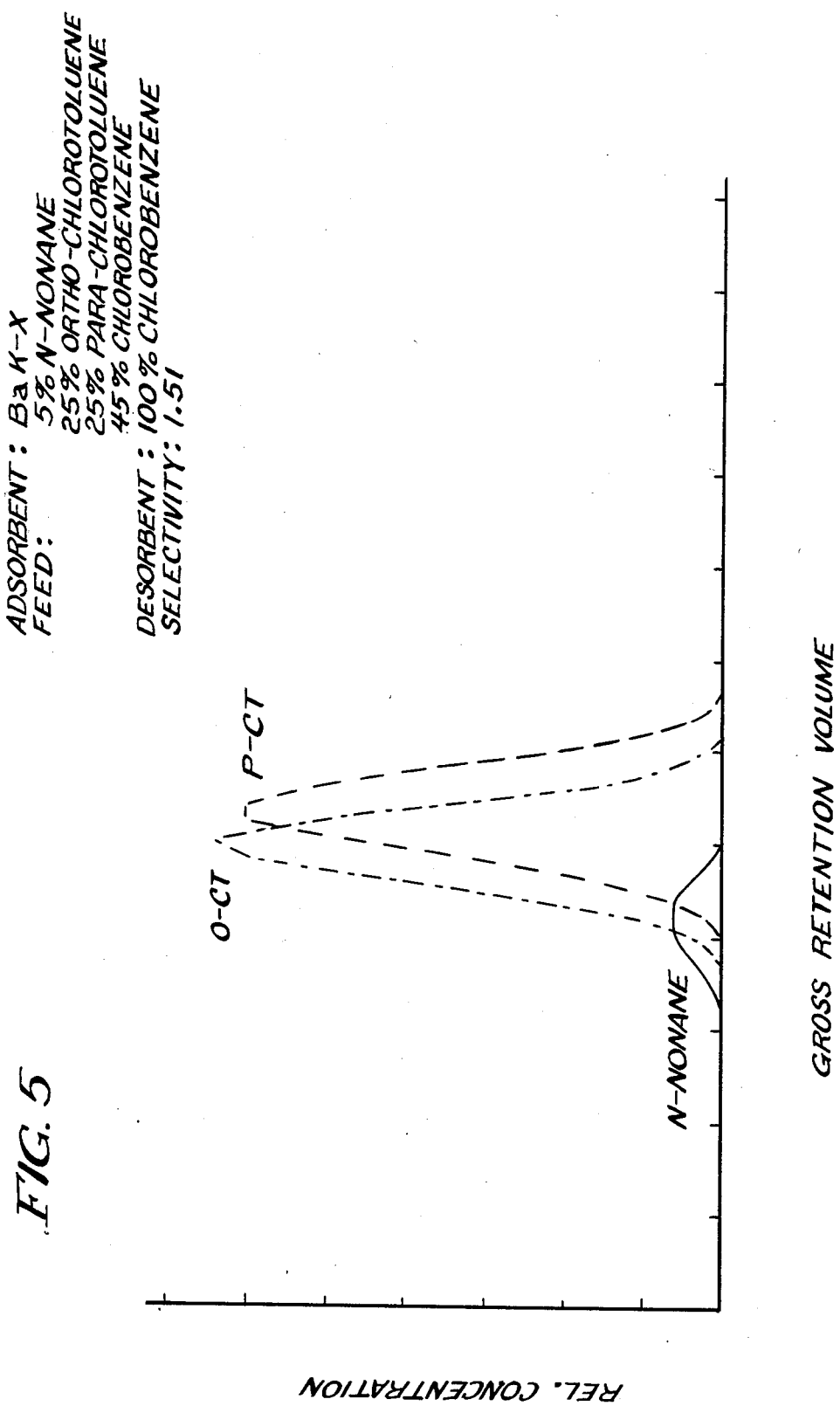

Component curves set forth in FIG. 4 show a clear and distinct separation of parachlorotoluene from the other feed components with a less distinct separation appearing in FIG. 5. In these cases parachlorotoluene is the last component to elute from each pulse test which is indicative of the most selectively retained component. Again the good selectivity of 1.98 for parachlorotoluene calculated from Test 4 exceeds the 1.51 selectivity obtained in Test 5. These selectivities quantitatively establish the superiority of applicant's desorbent with other adsorbents.

EXAMPLE IV

Figure 6:
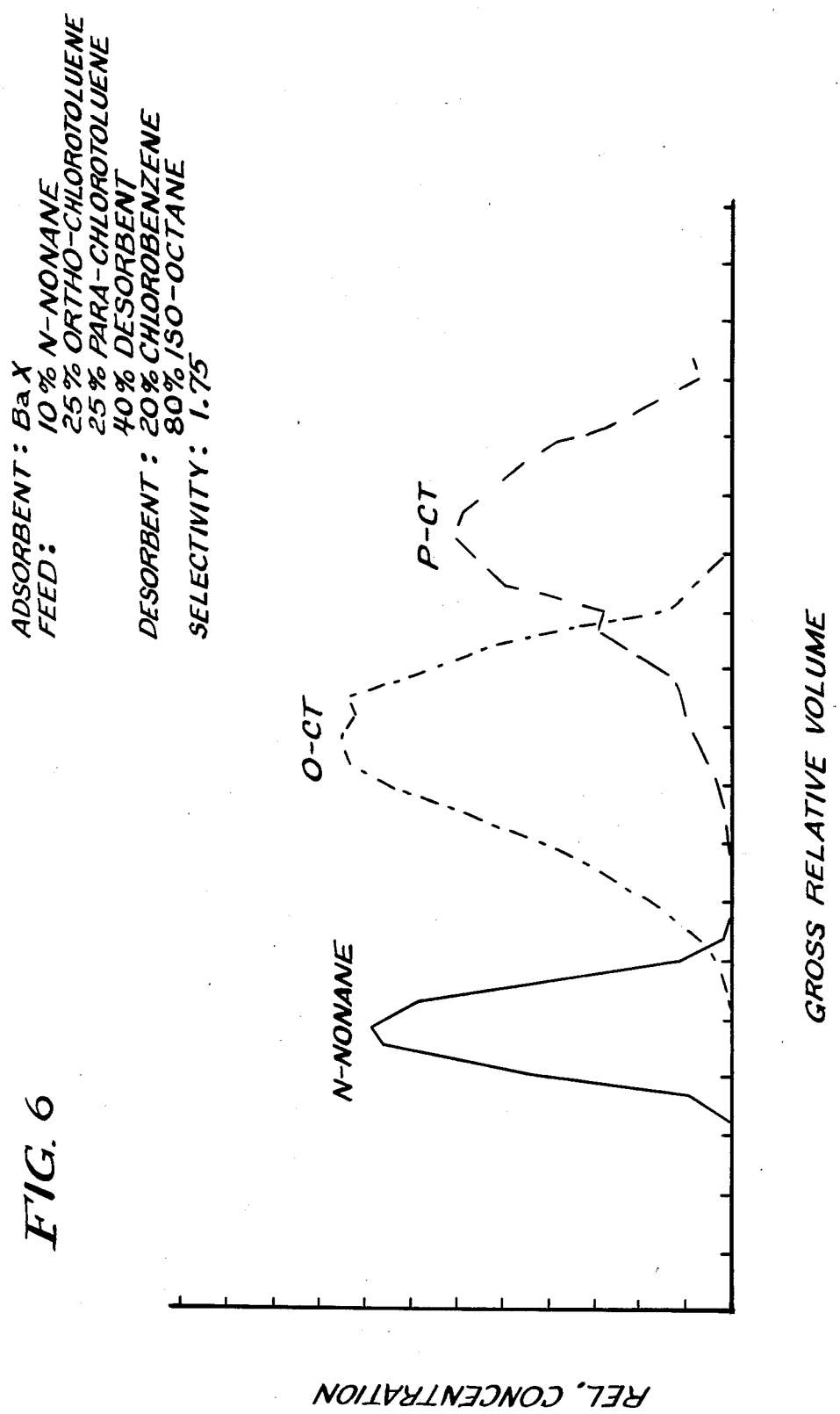

In this experiment, a sixth pulse test was performed to evaluate the desorbent material of this invention with an X type zeolite containing barium cations at cation exchange sites. The conditions and method of operation for this experiment were substantially the same as those previously described. The feed material mixture contained 25 vol. % orthochlorotoluene, 25 vol. % parachlorotoluene, 10 vol. % normal nonane and 40 vol. % desorbent material. The adsorbent material was a mixture of 20 vol. % chlorobenzene and 80 vol. % isooctane. FIG. 6 contains the tracings from this pulse test which show a distinct separation of the components.

EXAMPLE V

The separation of bromine substituted toluene isomers was investigated in the following experiments.

In these pulse tests, the column was again filled with a type X zeolite which in Tests 7 and 8 contained calcium cations at cation exchange sites and in Tests 9 and 10 contained barium and potassium cations at cation exchange sites. The feed mixture employed for this test contained about 10 vol. % normal nonane, 25 vol. % orthobromotoluene, 25 vol. % parabromotoluene and 40 vol. % desorbent material. The desorbent material for each test had the following compositions:

| Test | Desorbent |
|---|---|
| 7 | 30 vol. % chlorobenzene |
|   | 70 vol. % n-hexane |
| 8 | 100 vol. % chlorobenzene |
| 9 | 30 vol. % chlorobenzene |
|   | 70 vol. % n-hexane |
| 10 | 20 vol. % chlorobenzene |
|   | 80 vol. % isooctane |

Figure 7:
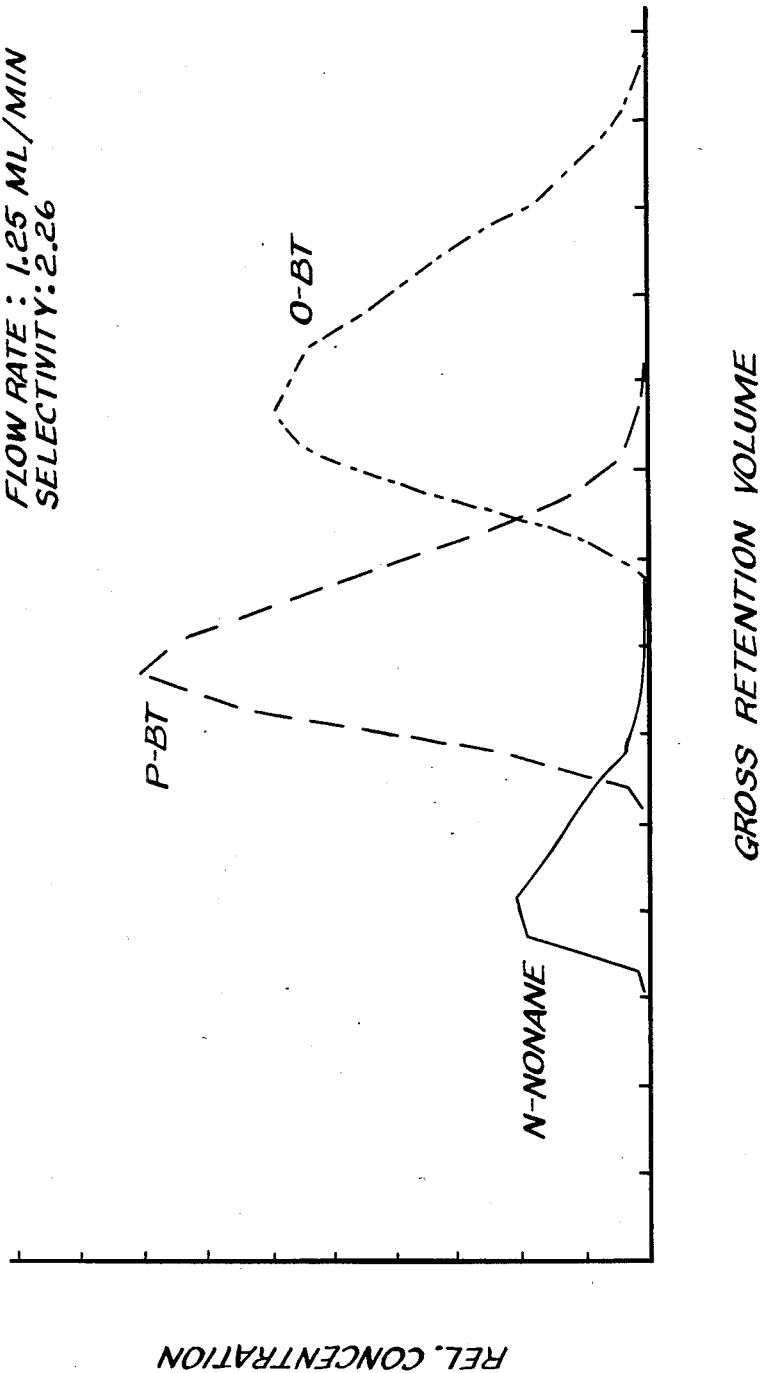
Figure 8:
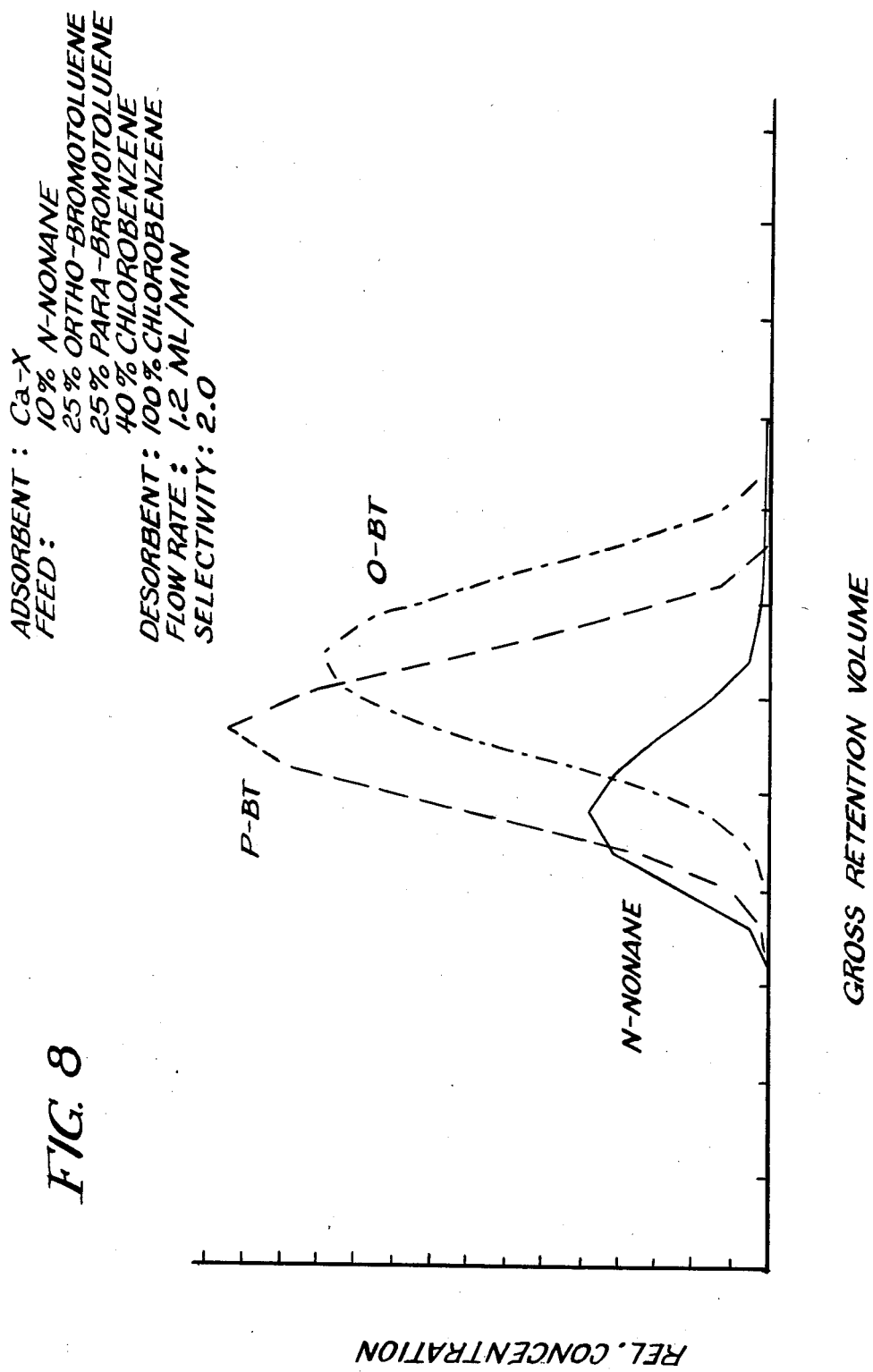
Figure 9:
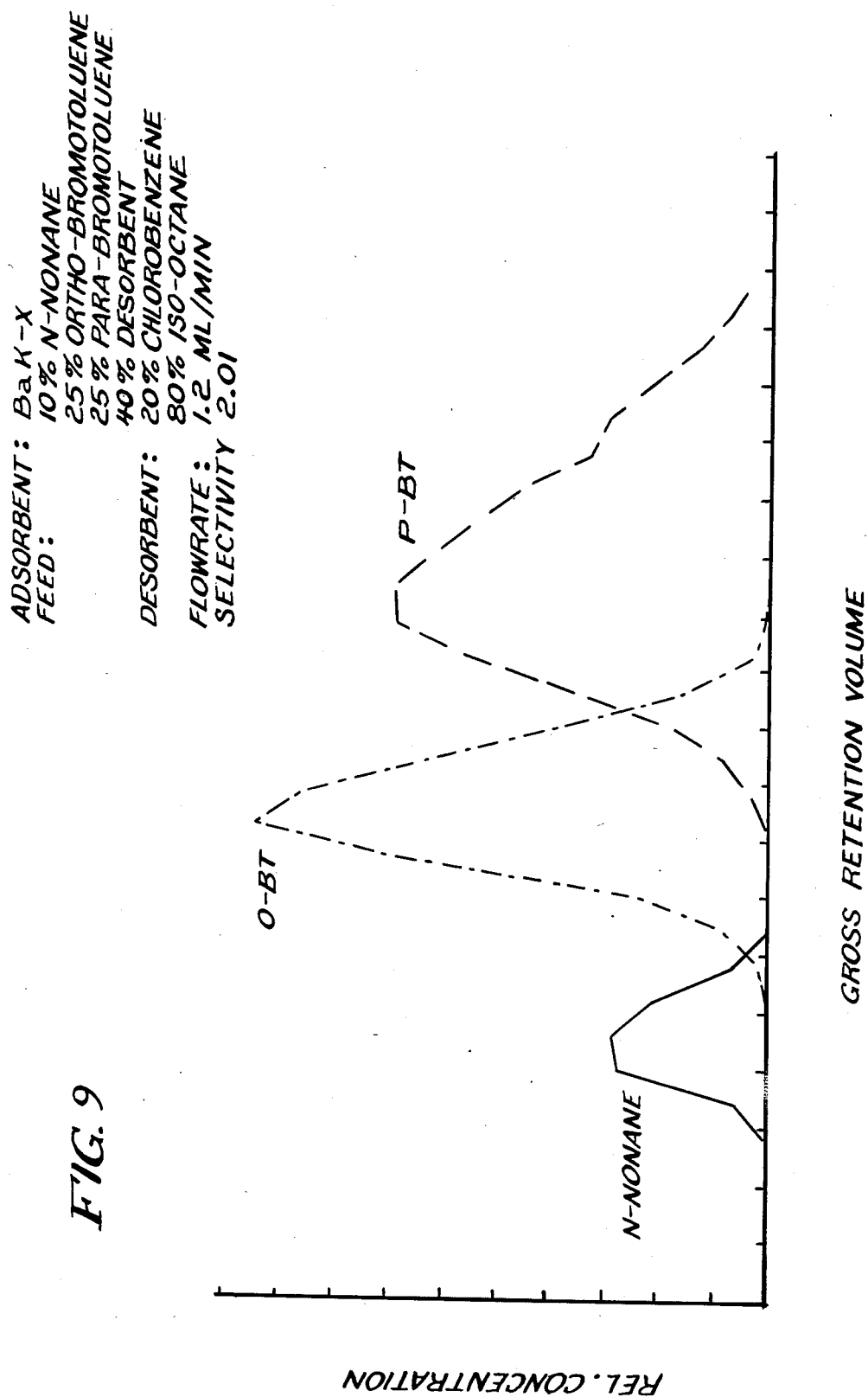
Figure 10:
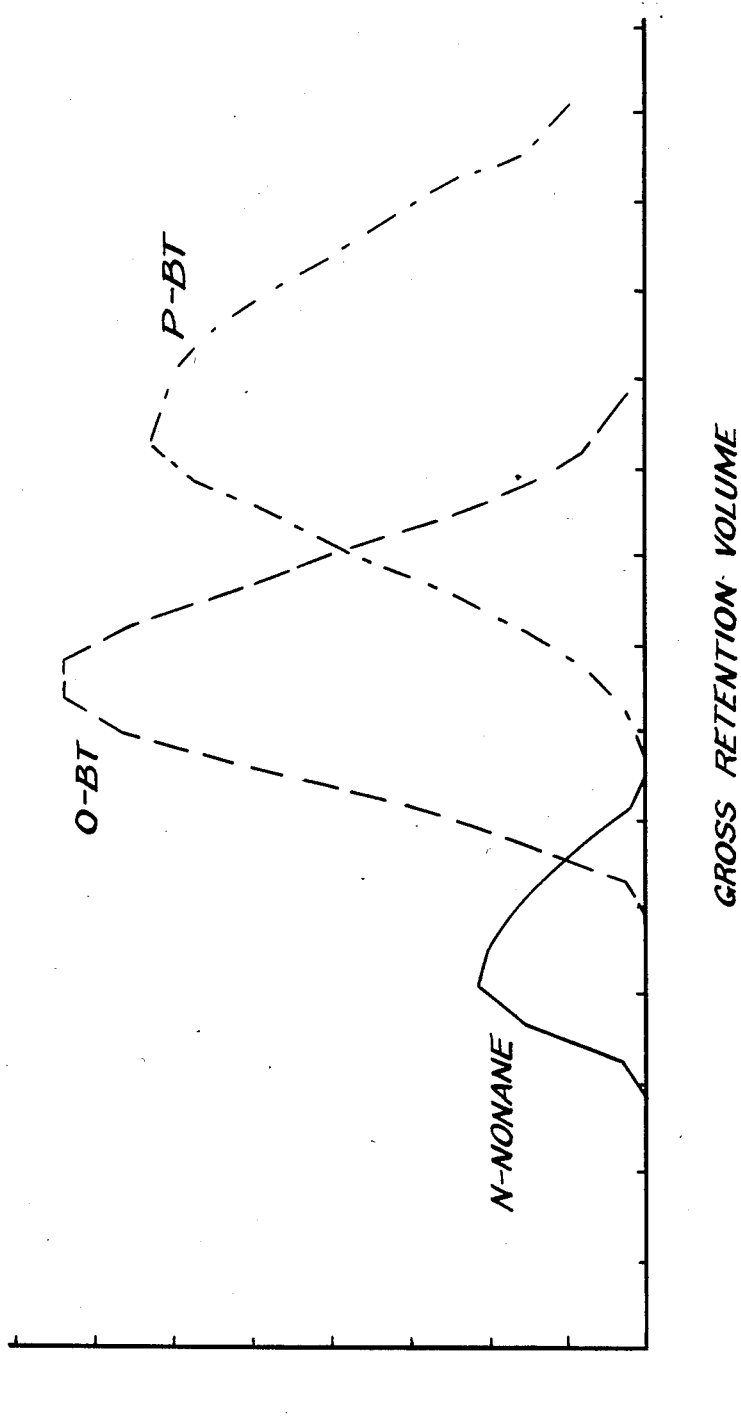

The operations taking place for each test were the same as those previously described. The chromatograph tracings obtained are shown in the attached FIGS. 7-10. A comparison of FIGS. 7 and 8 demonstrates that for the bromotoluene isomers combining a hydrocarbon, in this case normal hexane, with chlorobenzene provides a mixed desorbent which substantially improves the selectivity of adsorption/desorption systems when compared to the use of chlorobenzene alone. It can also be seen that the calcium exchanged X type zeolite again selectively retains the ortho isomer as was demonstrated in Example I. FIGS. 9 and 10, depicting the results for pulse tests 9 and 10, establish that the X type zeolite containing barium and potassium cations is highly para selective with respect to bromotoluene isomers as well as chlorotoluene isomers. More importantly, FIGS. 9 and 10 show that equivalent results may be obtained with different ratios and types of hydrocarbon components.

We claim as our invention:

1. A process for separating the para and ortho isomers of halogen substituted toluenes selected from the group consisting of chlorotoluene and bromotoluene from a feed mixture comprising said isomers which process comprises contacting said feed mixture at adsorption conditions, with an adsorbent comprising an X type zeolite having cations selected from the group consisting of calcium, barium, potassium and combinations thereof at cation exchange sites, selectively adsorbing one isomer to the substantial exclusion of the other isomer on said adsorbent, removing the nonadsorbed portion of the feed mixture from contact with the adsorbent, and thereafter recovering the adsorbed isomer from the adsorbent by contacting said adsorbent, at desorption conditions, with a desorbent composition consisting essentially of chlorobenzene and/or bromobenzene and a saturated aliphatic hydrocarbon having less than 9 carbon atoms, said saturated aliphatic hydrocarbon being present in said desorbent composition in an amount ranging from 60 to 90 percent by volume.

2. The process of claim 1 wherein said aliphatic hydrocarbon comprises isooctane or n-hexane.

3. The process of claim 1 wherein said adsorption conditions include a temperature in the range of about 20° C. to about 250° C. and a pressure sufficient to maintain liquid phase.

4. The process of claim 1 wherein said separation is effected by means of a simulated moving bed flow scheme.

5. The process of claim 4 wherein the simulated moving bed uses a countercurrent flow scheme.

6. The process of claim 4 wherein the simulated moving bed uses a cocurrent flow scheme.

7. A process for the separation of the ortho isomers of chloro or bromotoluene from a feed mixture comprising both ortho and para isomers of chloro or bromotoluene, which process comprises contacting said feed mixture, at adsorption conditions, with an adsorbent comprising an X type zeolite having calcium cations at cation exchange sites, selectively adsorbing said ortho isomer on said adsorbent, removing the nonadsorbed portion of the feed mixture from contact with the adsorbent and thereafter recovering said adsorbed ortho isomer by contacting the ortho isomer-containing adsorbent, at desorption conditions, with a desorbent composition consisting essentially of chlorobenzene and a saturated aliphatic hydrocarbon having less than 9 carbon atoms, said saturated aliphatic hydrocarbon being present in said desorbent composition in an amount ranging from 60 to 90 percent by volume.

8. The process of claim 7 wherein said aliphatic hydrocarbon comprises isooctane or n-hexane.

9. The process of claim 14 wherein said aliphatic hydrocarbon comprises isooctane.

10. The process of claim 9 wherein said aliphatic hydrocarbon comprises isooctane.

11. A process for the separation of a para isomer of chloro or bromotoluene from a feed mixture comprising both ortho and para isomers of chloro or bromotoluene which process comprises contacting said feed mixture at adsorption conditions with an adsorbent comprising an X type zeolite containing potassium and barium cations at cation exchange sites, selectively adsorbing said para isomer on said adsorbent, removing the nonadsorbed portion of the feed mixture from contact with the adsorbent and thereafter recovering said adsorbed para isomer by contacting the para isomer-containing adsorbent, at desorption conditions, with a desorbent composition consisting essentially of chlorobenzene and a saturated aliphatic hydrocarbon having less than 9 carbon atoms, said saturated aliphatic hydrocarbon being present in said desorbent composition in an amount ranging from 60 to 90 percent by volume.

* * * * *